United States Patent [19]

Togiya et al.

[11] Patent Number: 5,567,419
[45] Date of Patent: Oct. 22, 1996

[54] STABILIZED COSMETIC COMPOSITIONS CONTAINING MONOACYL PHOSPHATIDE AND A SAPONIN

[75] Inventors: Satoshi Togiya; Satomi Yamada; Mitsuo Kondo, all of Kanagawa, Japan

[73] Assignee: Kanebo Ltd., Tokyo, Japan

[21] Appl. No.: 627,694

[22] Filed: Dec. 14, 1990

Related U.S. Application Data

[63] Continuation-in-part of Ser. No. 454,157, Dec. 21, 1989, abandoned.

[30] Foreign Application Priority Data

Dec. 22, 1988 [JP] Japan ................................. 63-321940
Sep. 26, 1989 [JP] Japan ................................. 1-249983

[51] Int. Cl.$^6$ .............................. A61K 7/06; A61K 7/48; A61K 35/78; A61K 47/24
[52] U.S. Cl. ..................... 424/74; 424/70.21; 424/70.23; 514/786; 514/975; 514/846
[58] Field of Search ............................... 424/63, 73–74, 424/195.1, 70.21, 70.23; 514/784, 786, 788, 844–848, 936–43, 968, 975

[56] References Cited

U.S. PATENT DOCUMENTS

| | | | |
|---|---|---|---|
| 3,883,670 | 5/1975 | Pennings et al. | 426/613 |
| 4,034,124 | 7/1977 | van Dam | 426/605 |
| 4,115,598 | 9/1978 | Moran | 426/662 |
| 4,424,204 | 1/1984 | Minamino et al. | 514/943 |
| 4,568,667 | 2/1986 | Shirakawa et al. | 514/26 |
| 4,701,322 | 10/1987 | Dixon et al. | 424/70 |
| 4,800,080 | 1/1989 | Grollier et al. | 424/71 |
| 4,849,132 | 7/1989 | Fujita et al. | 426/654 |

FOREIGN PATENT DOCUMENTS

| | | |
|---|---|---|
| 0245871 | 11/1987 | European Pat. Off. . |
| 0255937 | 2/1988 | European Pat. Off. . |
| 0283713 | 9/1988 | European Pat. Off. . |
| 6017390 | 12/1986 | Japan . |
| 505983 | 5/1939 | United Kingdom . |

*Primary Examiner*—Edward J. Webman
*Attorney, Agent, or Firm*—Kane, Dalsimer, Sullivan, Kurucz, Levy, Eisele and Richard, LLP

[57] ABSTRACT

A cosmetic composition contains saponin and/or diacyl phosphatide in addition to monoacyl phosphatide, which shows improved storage stability at high and low temperatures, organoleptic properties and appearance.

6 Claims, No Drawings

STABILIZED COSMETIC COMPOSITIONS CONTAINING MONOACYL PHOSPHATIDE AND A SAPONIN

CROSS-REFERENCE TO RELATED APPLICATION

This application is a Continuation-In-Part of our copending U.S. patent application Ser. No. 07/454,157 filed Dec. 21, 1989, now abandoned.

BACKGROUND OF THE INVENTION

1. Field of the Invention

This invention relates to a cosmetic composition, particularly those containing at least one saponin or diacyl phosphatide in combination with monoacyl phosphatide.

2. Description of the Prior Art

There has recently been much research on emulsification and solubilization. As a result, improvement is seen in emulsifiers and solubilizers as well as technology of emulsification and solubilization. Now, stable emulsions and solubilized materials are being used in many fields.

Most of those emulsifiers and solubllizers are nonionic surface active agents having polyoxyethylene chains, anionic surface active agents such as fatty acid soaps, cationic surface active agents and amphoteric surface active agents. However, emulsified cosmetics and solubilized clear cosmetics in which those synthetic surface active agents are used generally have the drawback that they often stimulate the to skin and hair.

Under the above circumstances, phosphatide, particularly monoacyl phosphatide, has drawn attention. Japanese Patent Application Laid-Open 112007/86 discloses clear cosmetic compositions in which monoacyl phosphatide is used as a solubilizer. Japanese Patent Application Laid-Open 171407/86 discloses emulsion cosmetic compositions in which monoacyl phosphatide is used as an emulsifier.

However, the previous clear cosmetic compositions and emulsion cosmetic compositions in which monoacyl phosphatide is used have a problem with storage stability, particularly in low and high temperature conditions. In addition, further improvement is needed in organoleptic properties, particularly continued smoothness, and appearance such as texture and clearness.

That is, when clear cosmetic compositions are stored at a low temperature (below 5° C.) or high temperature (above 40° C.), monoacyl phosphatide tends to precipitate or cause turbidity. When emulsion cosmetic compositions are stored at a low or high temperature, viscosity and appearance such as texture change disadvantageously.

Meanwhile, saponin is a compound in which a nonpolar group (saponigen) such as sterol or triterpene is bound to saccharide such as penrose, hexose or uronic acid. They are found broadly in various plants besides certain type of asteroids. More than one types of saponin often exists in a single plant. Saponin has been studied as a medicamental component in recent years, but only a few cosmetic compositions are known in which saponin is used. It is suggested to use a saponin component of licorice, i.e., glycyrrhizin, in a cosmetic composition from a viewpoint of its anti-inflammatory effect, anti-allergic effect, antigen antibody suppression effect and steroid hormonic effect (Fragrance Journal, Vol. 3, No. 4, 39–41, 1975, Japan). It is known that in a skin cosmetic containing an oil obtained from seed of Oenothera tetraptera Cav., an extract from seed of Helianthus annuus L., root of Bupleurum falcatum L. or rhizome of Sanguisorba officinalis L. is blended as a stabilizer to prevent acidification or oxydation of the oil, and the extract contains saponin (Japanese Patent Application Laid-Open 178908/86). A shampoo is known in which a main component is an aqueous extract from pericarp of Sapindus mukurosii. This is said to have practically sufficient foaming ability and detergency (Japanese Patent: Application Laid-Open 125510/77). A hair tonic containing an extract from crude drugs such as Chinese matrimony vine is known in which polyoxyethylene-hardened castor oil, polyoxyethylene sorbitan sesquioleate or polyoxyethylene sorbitan monostearate is used as an emulsifier or solubilizer (Japanese Patent Publication 40923/83).

Meanwhile, diacyl phosphatide has been used as a wetting agent or emulsifier in the fields of foodstuffs, pharmaceuticals, cosmetics and the like, because it has a highly lipophilic fairy acid on its one end and a highly hydrophilic choline structure on another end and is, therefore, amphipathic. However, its emulsifying ability is not sufficient for some oily substances and, therefore, a prepared oil-in-water emulsion may cause phase inversion into a water-in-oil emulsion around room temperature or may have poor appearance or poor emulsion properties.

U.S. Pat. No. 3,652,397 discloses a process for the preparation of a lisophosphatide emulsifying agent by partially hydrolysing phosphatide obtained from soyabean, etc. This emulsifying agent contains unreacted phosphatide, i.e. diacyl phosphatide, besides the reaction product lysophosphatide, i.e. monoacyl phosphatide. The above U.S. Pat. No. 3,652,397 discloses the application of the lysophosphatide emulsifying agent mostly in foodstuffs such as margarine and mayonnaise. Except for just one line, "cosmetic preparations, for example lotions and salves", there is no concrete disclosure on cosmetic compositions. In reality, clear lotions cannot be obtained by the use of diacyl phosphatide. The U.S. Patent does not suggest that emulsion cosmetic compositions in which a combination of monoacyl phosphatide and diacyl phosphatide is used, show unexpectedly high stability during storage, improved organoleptic properties and appearance.

SUMMARY OF THE INVENTION

The present inventors have conducted keen research to solve the aforesaid drawback of cosmetic compositions in which monoacyl type phosphatide is used and have now found that when monoacyl type phosphatide is used in combination with saponin or diacyl type phosphatide, precipitation or turbidity does not occur during storage, and organoleptic properties and appearance are improved.

The effects attained by the above combination could not be expected.

Thus, the present invention provides a cosmetic composition comprising an oily substance and water, characterized in that the cosmetic composition further contains at least one monoacyl type phosphatide represented by the following general formula (1) or (2):

$$\begin{array}{l} CH_2-O-R \\ | \\ CH-OH \\ | \\ CH_2-X \end{array} \quad (1)$$

-continued $$CH_2-OH \qquad (2)$$
$$CH-O-R$$
$$CH_2-X$$

wherein R represents

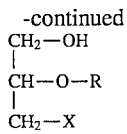

$-C-C_{17}H_{35}$ or $-C-C_{15}H_{31}$,
with C=O double bonds and X represents

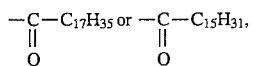

$$-O-\overset{O}{\underset{O^{\ominus}}{P}}-O-CH_2-CH_2-N^{\oplus}(CH_3)_3,$$

$$-O-\overset{O}{\underset{O^{\ominus}}{P}}-O-CH_2-CH_2-N^{\oplus}H_3 \text{ or}$$

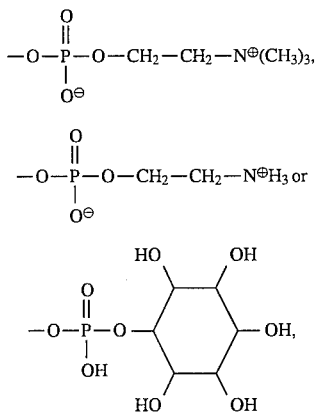

phosphate linked to inositol ring with HO, OH substituents and at least one substance selected from the group consisting of saponin and diacyl type phosphatide.

DETAILED DESCRIPTION OF THE INVENTION

The compounds represented by the aforesaid general formula (1) or (2) in the invention, i.e. mono-O-acyl-3-glyceryl phosphoryl choline, mono-O-acyl-3-glyceryl phosphoryl ethanolamine and mono-O-acyl-3-glyceryl phosphoryl inositol are publicly known per se. The compounds represented by the general formula (1) include 1-palmitoyl-3-glyceryl phosphoryl choline, 1-stearoyl-3-glyceryl phosphoryl choline, 1-palmitoyl-3-glyceryl phosphoryl ethanolamine, 1-stearoyl-3-glyceryl phosphoryl ethanolamine, 1-palmitoyl-3-glyceryl phosphoryl inositol, and 1-stearoyl-3-glyceryl phosphoryl inositol. The compounds represented by the general formula (2) include 2-palmitoyl-3-glyceryl phosphoryl choline, 2-stearoyl-3-glyceryl posphoryl choline, 2-palmitoyl-3-glyceryl phosphoryl ethanolamine, 2-stearoyl-3-glyceryl phosphoryl ethanolamine, 2-palmitoyl-3-glyceryl phosphoryl inositol, and 2-stearoyl-3-glyceryl phosphoryl inositol.

The compounds represented by the general formula (1) or (2) may be prepared by treating a starting material phosphatidyl choline, phosphatidyl ethanolamine or phosphatidyl inositol obtained from, for instance, yolk with snake venom phospholipase or enzyme extracted from swine pancreas, i.e. pancreatin, and then fractioning it with high performance liquid chromatography. Alternatively, the compounds may be chemically synthesized.

The compounds represented by the general formula (1) or (2) are safe to a human body. When their stimulus to skin was tested in accordance with Draize's method, the score of animal skin stimulus and the score of human skin stimulus were both zero, which means that they are non-stimulative, [Draize, J. H., Association of Food and Drug officials of the United States. "Appraisal of the Safety of Chemicals in Foods, Drugs and Cosmetics", 46(1959), Texas, State Department of Health, Austin.]

One or more of the compounds represented by the above general formula (1) or (2) according to the invention may be used alone or in combination as an emulsifier or solubilizer.

Saponin or saponin-containing plant extracts used in the invention are publicly known.

As stated above, saponin used in the invention is defined as a compound composition of a hydrophobic moiety selected from sterol or triterpene and a hydrophilic saccharide moiety. These moieties are bound by glycosidic linkage with each other. They are found broadly in various plants besides certain types of asteroids. More than one type of saponin exists in a single plant. Although the present invention should not be particularly limited by %heir sources or acquisition methods, saponin-containing sources include Ophiopogonis tuber, Asparagi radix, Ptytolaccae radix, Senegae radix, Polygalae radix, Ginseng radix (Pharmacia, Vol. 15, No. 10, 897–899, 1979, Japan), Glycyne max Merrill (Japanese Patent Application Laid-Open 150981/81), Gynostenma pentaphyllum MAKINO (Japanese Patent Application Laid-Open 127318/81), licorice (Fragrance Journal, Vol. 3, No. 4, 39– 41, 1975, Japan), seed of Hetianthus annuus L., root of Bupleurum falcatum L., rhizome of Sanguisorba officinalis L. (Japanese Patent Application Laid-Open 178908/89), pericarp of Sapindus mukurosii (Japanese Patent Application Laid-Open 125510/77), roots of Bupleurum falcatum L., etc. (Japanese Patent Publication 10923/67), Cirsium mill, Chinese matrimony vine, Bupleurum falcatum L. and Cnidium officinale Makino (Japanese Patent Publication 40923/83), senega, Hamamelis virginiana, Potentilla wallichiana Del. and Althaea officinalis (Japanese Patent Application Laid-Open 106607/82). In the present invention, saponin-containing plant extracts obtained by extracting the aforesaid plants in any known method, or purified saponin therefrom may be used.

Particularly preferred examples include saponin obtained from licorice ($\alpha$- or $\beta$-glycyrrhizin or derivatives thereof), an extract from pericarp of Sapindus mukurosii, soyabean saponin, extract from rhizome of Sanguisorba officinalis L., extract from seed of Thea sinensis, L. and extract from seed of camellia.

Both clear cosmetic compositions and emulsion cosmetic compositions may be prepared using a combination of the compound represented by the above formula (1) or (2) with saponin without a substantial amount of diacyl phosphatide.

The amount of the compound represented by the above formula (1) or (2) used and the amount of the above saponin or saponin-containing extract (as a saponin content) used are both about 0.01 to about 10% by weight, preferably 0.1 to 5% by weight, based on the total weight of a cosmetic composition.

If even either of the compound of formula (1) or (2) and saponin is used in an amount less than the aforesaid amount, storage stability of a cosmetic composition is poor. On the other hand, if they are used in an amount larger than the above amount, they do not completely dissolve in the system and tend to separate, and further the feel of the use of a cosmetic composition tends to worsen.

Emulsion cosmetic compositions may be prepared using a combination of the monoacyl phosphatide represented by the above formula (1) or (2) with the diacyl phosphatide.

The diacyl phosphatide may be represented by those of the following formulae:

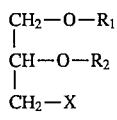

wherein $R_1$ is

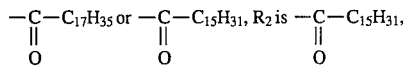

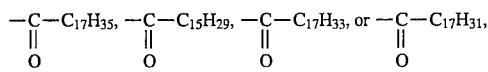

and X is

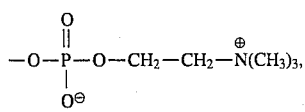

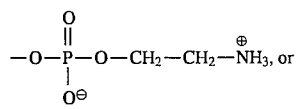

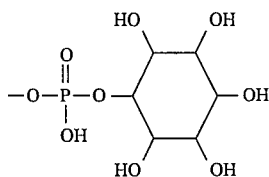

The diacyl phosphatide used in the invention exist generally and are known as an important component of vital membranes. In the invention, its source or aquisition method is not particularly limited, but brains and livers of animals, yolk, soyabean and yeast may be named. In the invention, it is possible to use a diacyl phosphatide-containing extract obtained by extracting the aforesaid animals, vegetation in any known method, or purified diacyl phosphatide therefrom. Synthetic diacyl phosphatide may also be used.

Examples of the diacyl phosphatide include 1,2-dipalmitoyl-3-glyceryl phosphoryl ethanolamine, 1,2-dipalmitoyl-3-glyceryl phosphoryl choline, 1-oleoyl-2-stearoyl-3-glyceryl phosphoryl choline, 1,2-dihexadecenyl-3-glyceryl phosphoryl ethanolamine, 1,2-dioleoyl-3-glyceryl phosphoryl choline, 1-palmitoyl-1-oleoyl-3-glyceryl phosphoryl ethanolamine, 1,2-distearoyl-3-glyceryl phosphoryl inositol, 1-palmitoyl-2-stearoyl-3-glyceryl phosphoryl ethanolamine, and 1-stearoyl-2-palmitoyl-3-glyceryl phosphoryl inositol.

The used amount of the monoacyl phosphatide represented by formula (1) or (2) is preferably 0.01 to 10% by weight, more preferably 0.1 to 5% by weight, and the amount of the aforesaid diacyl phosphatide is preferably 0.001 to 10% by weight, more preferably 0.01 to 5% by weight, based on the total weight of the formulation.

If even either of the monoacyl phosphatide represented by formula (1) or (2) and the diacyl phosphatide is used in an amount less than the aforesaid amount, the desired storage stability is not attained sometime. On the other hand, if they are used in an amount larger than the above amount, they themselves do not completely dissolve in the system and tend to separate, and further the feel of the use of a cosmetic composition tends to worsen.

The terms "oily substance" as used herein mean, generally, oily substance, such as oil-soluble perfumes, oil-soluble vitamins, oil-soluble hormones, oil-soluble colors, oil-soluble UV absorbers, higher aliphatic hydrocarbons, vegetable oils, animal oils, waxes, higher fatty acids, higher alcohols and synthetic ester oils.

More specifically, the oil-soluble perfumes include those extracted from natural animals or plants and synthetic ones. The oil-soluble vitamins include vitamins A, D, E, F and K, vitamin derivatives such as pyridoxine dicaprylate, pyridoxine dipalmitate, dl-α-tocopherol acetate, dl-α-tocopherol nicotinate, ascorbyl dipalmitate, ascorbyl monopalmitate and ascorbyl monostearate. The oil-soluble hormones include estradiol, ethinyl estradiol, estrone and diethylstilbestrol. The oil-soluble colors include Sudan III, tetrabromofluoresceine, dibromofluorescein, fluorescein and quinizarin green SS. The oil-soluble UV absorbers include oxybenzone and methyl 2,5-diisopropyl cinnamate.

The higher aliphatic hydrocarbons include liquid paraffin, squalane, microcrystalline wax, vaseline and ceresin. The vegetable oils include olive oil, castor oil, cacao oil and palm oil. The animal oils include cod liver oil, beef tallow and butter oil. The waxes include bees wax and carnauba wax. The higher fatty acids include lauric acid, myristic acid, paimitic acid, stearic acid, oleic acid, behenic acid and ianolin fatty acid. The higher alcohols include lauryl alcohol, stearyl alcohol, cetyl alcohol and oleyl alcohol. The synthetic ester oils include linear or branched esters such as butyl stearate, hexyl laurate, octyl dodecyl myristate, diisopropyl adipate and diisopropyl sebacate.

One or mote of these oily substances may be used alone or in combination.

In the cases of clear cosmetic compositions such as lotions and hair tonics, the used amount of the oily substance ranges from about 0.0001 to about 1% by weight, preferably from about 0.001 to about 0.3% by weight, based on the total weight of whole formulation. If the amount is less than about 0.0001% by weight, intrinsic effects of the oily substance in question are insufficiently exhibited. If it exceeds about 1% by weight, the substance tends to be difficultly solubilized.

In the cases of emulsion cosmetic compositions such as creams and milky lotions, the amount of the oily substance used ranges from about 3 to about 80% by weight, preferably from about 10 to about 60% by weight, based on the total weight of whole formulation of the emulsion composition. If the amount is less than about 3% by weight, storage stability is a little poor and the finishing touch is more refreshing than expected with an emulsion cosmetic. If it exceeds about 80% by weight, the composition has a greasy feel which is undesirable.

To the cosmetic composition according to the invention may be added humectants, medicinal components for beauty, perfumes, antiseptics, colorants, UV absorbers, astringents, synthetic surface active agents, pigments such as kaolin, mica, sericite, talc, yellow iron oxide and red iron oxide, water-soluble natural high molecular substances such as casein soda, pectin, xanthan gum, karaya gum, locust bean gum and carrageenan, if needed.

Examples of the cosmetic composition according to the invention include skin treatment lotions, facial fresheners, softening lotions, acne treatment lotions, after-shave lotions, conditioning lotions containing pigments or powder, cleansing lot ions, hair tonics, massage creams, cleansing creams, skin creams, skin milks, foundation creams, make-up bases and hair creams, but the invention is not limited to these.

EXAMPLES

Preferred embodiments of the invention will be explained below.

"Part" hereinafter means part by weight.

The properties of cosmetic compositions examined in the Examples were storage stability, organoleptic properties, pH, clearness and appearance. The testing methods are as follows.

(1) Storage stability

Sample compositions are allowed to stand in a thermostatic chamber at a temperature of 45° C., 40° C., 30° C., 5° C. or 0° C. for 3, 4 or 6 months, and the viscosity and the presence of precipitates are examined.

(2) Organoleptic properties

Feels of the application such as refreshing feel, moistening feel, greasy feel and smoothness, and finishing after the application are examined by three specialists and overall evaluation is made.

(3) Determination of pH

A pH value is determined immediately after the preparation of a cosmetic composition. A pH-measuring unit with a glass electrode is well adjusted using a standard pH liquid and then used.

(4) Clearness

Clearness is expressed by transmittance of light of 450 nm wave length. When the value is 80% or higher, a substance is visually transparent.

(5) Appearance

Color or texture is visually evaluated.

EXAMPLES 1 TO 5 AND COMPARISON EXAMPLES 1 AND 2

Cosmetic lotions were prepared with the formulations shown in Table 1 (part by weight). 1-Palmitoyl-3-glyceryl phosphoryl choline was used as phosphatide. The used licorice saponin was commercially bought and contained α-glycyrrhizin mainly.

Ingredients 1 to 3 shown in Table 1 were mixed to dissolve, which was called solution 1. Separately, ingredients 4 to 7 shown in Table 1 were mixed to dissolve, which was called solution 2. Solutions 2 was admixed to solution 1 to prepare a cosmetic lotion. The properties of the resulting cosmetic lotion are as shown in Table 1.

As seen from the Table, the cosmetic lotions which contained both phosphatide and saponin as the Examples of the invention showed excellent storage stability. In contrast, the cosmetic lotions of Comparison Examples 1 and 2 which lacked either one of phosphatide or saponin showed poor storage stability to cause precipitation, turbidity and floating oil. The cosmetic lotions of the invention were superior to those of the Comparison Examples also in the organoleptic properties and clearness.

TABLE 1

| Ingredient | Ex. 1 | Ex. 2 | Ex. 3 | Ex. 4 | Ex. 5 | Comp. 1 | Comp. 2 |
|---|---|---|---|---|---|---|---|
| 1. 1-Palmitoyl-3-glyceryl phosphoryl choline | 0.01 | 0.1 | 1.0 | 5.0 | 10.0 | — | 0.1 |
| 2. Ethanol | 10.0 | 10.0 | 10.0 | 10.0 | 10.0 | 10.0 | 10.0 |
| 3. Bergamot oil | 0.04 | 0.04 | 0.04 | 0.04 | 0.04 | 0.04 | 0.04 |
| 4. Dipropylene glycol | 5.0 | 5.0 | 5.0 | 5.0 | 5.0 | 5.0 | 5.0 |
| 5. Licorice saponine (α-glycyrrhizin) | 0.1 | 0.1 | 0.1 | 0.1 | 0.1 | 0.1 | — |
| 6. Disodium hydrogenphosphate | 0.012 | 0.008 | 0.003 | 0.022 | 0.067 | 0.015 | 0.002 |
| 7. Purified water | 84.838 | 84.752 | 83.857 | 79.838 | 74.793 | 84.845 | 84.858 |
| Storage stability (precipitation) 0° C., 3 months | G | G | G | G | G | T | T |
| 45° C., 3 months | G | G | G | G | G | O | P |
| Organoleptic properties | G | G | G | G | Slightly G | Slightly G | Greasy |
| Clearness immediately After preparation | 82 | 87 | 92 | 91 | 86 | 71 | 78 |
| 6 months after, 30° C. | 80 | 86 | 93 | 90 | 82 | 60 | 63 |
| pH | 5.5 | 5.5 | 5.5 | 5.5 | 5.5 | 5.5 | 5.5 |

G: Good, T: Turbid, O: Floating Oil, P: Precipitation

EXAMPLES 6 AND 10 AND COMPARISON EXAMPLES 3 AND 4

Skin milks were prepared with the formulations shown in Table 2 (part by weight).

2-Palmitoyl-3-glyceryl phosphoryl ethanolamine was used as phosphatide. A saponin-containing extract was used which was obtained by purifying an aqueous ethanol extract of pericarp of Sapindus mukurosii and drying it into powder. This contained 50 to 60% of saponin.

The oily ingredients 1 to 5 shown in the Table were mixed to dissolve homogeneously at about 80° C. (solution 1). The water-soluble ingredients 6 to 10 and were homogeneously dissolved at about 80° C. (solution 2). Solution 1 was added to solution 2 under stirring with a homomixer to emulsify, and then cooled. During this cooling step, ingredient 11 was added at a temperature of 70° C. When the temperature lowered to 30° C., the stirring was stopped.

The properties of the resulting skin milks are as shown in Table 2.

As seen from the Table, the skin milks which contained both phosphatide and saponin as the Examples of the invention showed excellent storage stability. In contrast, the skin milks of Comparison Examples 3 and 4 which lacked either one of phosphatide or saponin were unstable to show remarkable increase or decrease in viscosity during storage. The skin milks of the invention were highly superior to those of the Comparison Examples also in organoleptic properties and had good appearance.

TABLE 2

|  |  | Ex. 6 | Ex. 7 | Ex. 8 | Ex. 9 | Ex. 10 | Comp. 3 | Comp. 4 |
|---|---|---|---|---|---|---|---|---|
| 1. Glyceryl monostearate (self-emulsifying type) | | 1.0 | 1.0 | 1.0 | 1.0 | 1.0 | 1.0 | 1.0 |
| 2. Liquid paraffin | | 7.0 | 7.0 | 7.0 | 7.0 | 7.0 | 7.0 | 7.0 |
| 3. Octyl dodecyl myristate | | 3.0 | 3.0 | 3.0 | 3.0 | 3.0 | 3.0 | 3.0 |
| 4. Cholesterol | | 0.5 | 0.5 | 0.5 | 0.5 | 0.5 | 0.5 | 0.5 |
| 5. Cetyl alcohol | | 0.5 | 0.5 | 0.5 | 0.5 | 0.5 | 0.5 | 0.5 |
| 6. 2-Palmitoyl-3-glyceryl phosphoryl ethanolamine | | 1.0 | 1.0 | 1.0 | 1.0 | 1.0 | 1.0 | — |
| 7. Dipropylene glycol | | 5.0 | 5.0 | 5.0 | 5.0 | 5.0 | 5.0 | 5.0 |
| 8. Xanthan gum | | 0.2 | 0.2 | 0.2 | 0.2 | 0.2 | 0.2 | 0.2 |
| 9. Extract of pericarp of Sapindus mukurosii | | 0.01 | 0.1 | 0.5 | 1.0 | 7.0 | — | 0.5 |
| 10. Methyl-p-oxybenzoate | | 0.2 | 0.2 | 0.2 | 0.2 | 0.2 | 0.2 | 0.2 |
| 11. Perfume | | 0.1 | 0.1 | 0.1 | 0.1 | 0.1 | 0.1 | 0.1 |
| 12. Purified water | | 81.49 | 81.4 | 81.0 | 80.5 | 76.5 | 81.5 | 82.0 |
| Storage stability (viscosity, cps) | I.A.P. | 1500 | 1300 | 1800 | 2600 | 1400 | 700 | 1100 |
| | 5° C., 3 months | 4200 | 3800 | 4400 | 4700 | 3700 | 10000< | 10000< |
| | 40° C., 3 months | 900 | 1100 | 1200 | 1200 | 900 | 100> | separation |
| Organoleptic properties | | G | G | G | G | G | * | * |
| Appearance | I.A.P. | W | W | W | W | W | W | S.C. |
| | 6 months after, 30° C. | W | W | W | W | S.C. | W | S.C. |
| | pH | 6.5 | 6.5 | 6.3 | 6.3 | 6.3 | 6.7 | 6.0 |

I.A.P.: Immediately After Preparation, G: Good,
*: Slightly less smooth, W: white, S.C.: Slightly Colored

EXAMPLE 11 AND COMPARISON EXAMPLE 5

Skin creams were prepared with the following formulations (part by weight). 1-Stearoyl-3-glyceryl phosphoryl inositol was used as phosphatide, and soyabean saponin with a saponin content of about 80% was used as saponin.

|  | Ex. 11 | Comp. 5 |
|---|---|---|
| 1. Olive oil | 5.0 | 5.0 |
| 2. Liquid paraffin | 15.0 | 15.0 |
| 3. Bees wax | 3.0 | 3.0 |
| 4. Cetyl alcohol | 7.0 | 7.0 |
| 5. Glyceryl monostearate | 3.0 | 3.0 |
| 6. White vaseline | 3.0 | 3.0 |
| 7. 1-Stearoyl-3-glyceryl phosphoryl inositol | 0.5 | 0.5 |
| 8. 75% Maltitol solution | 10.0 | 10.0 |
| 9. Methl p-oxybenzoate | 0.2 | 0.2 |
| 10. Soyabean saponin | 0.5 | — |
| 11. Perfume | 0.1 | 0.1 |
| 12. Purified water | 52.7 | 53.2 |

Among the above ingredients the oily ingredients 1 to 6 were mixed to dissolve homogeneously at about 80° C. (solution 1). The water-soluble ingredients 7 to 10 and 12 were mixed to dissolve homogeneously at about 80° C. (solution 2). Solution 1 was added to solution 2 under stirring to emulsify, and then cooled. During this cooling step, ingredient 11 was added at a temperature of 70° C. When the temperature lowered to 30° C., the stirring was stopped.

The skin cream of Example 11 thus obtained was an o/w emulsion and showed very good stability after stored in a thermostatic chamber at 45° C. for 4 months. It was also very stable and caused no deterioration or odd odors after stored at 0° C. or 5° C. for 6 months. It had good appearance such as texture, and showed good feel, moisture retention, and application properties such as easiness of taking-up on fingers, and extending on skin.

The skin cream of Comparison Example 5 in which Example 11 was repeated without the soyabean saponin and with 53.2 parts of water was an o/w emulsion, and was unstable after stored in a thermostatic chamber at 45° C. for 4 months. After stored at 0° C. for 6 months, its texture became bad and no smoothness was left after application.

When extracts from licorice (β-glycyrrhizin), pericarp of Sapindus mukurosii, seed of tea trees, seed of camellia and rhizome of Sanguisorba officinalis L. were used in place of the soyabean saponin of Example 11, the prepared skin creams showed behavior almost similar to that of the skin cream of Example 11.

EXAMPLES 12 TO 17 AND COMPARISON EXAMPLES 6 AND 7

Skin milks were prepared with the formulations shown in Table 3 (part by weight).

2-Palmitoyl-3-glyceryl phosphoryl choline was used as monoacyl phosphatide.

1,2-Dipalmitoyl-3-glyceryl phosphoryl ethanolamine was used as diacyl phosphatide.

The oily ingredients 1 to 8 shown in the Table were mixed to dissolve homogeneously at about 80° C. (solution 1). The water-soluble ingredients 7 to 10 and 12 were homogeneously dissolved at about 80° C. (solution 2). Solution 1 was added to solution 2 under stirring to emulsify, and then cooled. During this cooling step, ingredient 11 was added at a temperature of 70° C. When the temperature lowered to 30° C., the stirring was stopped.

The properties of the resulting skin milks are as shown in Table 3.

The skin milks of Examples 12 to 17 showed excellent storage stability. In contrast, the skin milks of Comparison Examples 6 and 7 which lacked either one of monoacyl phosphatide or diacyl phosphatide showed remarkable increase in viscosity during the storage at 0° C. for 3 months, or caused phase separation during the storage at 45° C. for 3 months to prove unstable emulsification, respectively. The skin milks of the invention were highly superior to those of the Comparison Examples also in organoleptic properties and had good appearance.

TABLE 3

|  | Ex. 12 | Ex. 13 | Ex. 14 | Ex. 15 | Ex. 16 | Ex. 17 | Comp. 6 | Comp. 7 |
|---|---|---|---|---|---|---|---|---|
| 1. Glyceryl monostearate (self-emulsifying type) | 1.0 | 1.0 | 1.0 | 1.0 | 1.0 | 1.0 | 1.0 | 1.0 |
| 2. Liquid paraffin | 10.0 | 10.0 | 10.0 | 10.0 | 10.0 | 10.0 | 10.0 | 10.0 |
| 3. Squalane | 1.0 | 1.0 | 1.0 | 1.0 | 1.0 | 1.0 | 1.0 | 1.0 |
| 4. Cholesterol | 0.5 | 0.5 | 0.5 | 0.5 | 0.5 | 0.5 | 0.5 | 0.5 |
| 5. Cetyl alcohol | 0.1 | 0.1 | 0.1 | 0.1 | 0.1 | 0.1 | 0.1 | 0.1 |
| 6. 2-Dipalmitoyl-3-glyceryl phosphoryl ethanolamine | 1.0 | 1.0 | 1.0 | 1.0 | 1.0 | 1.0 | — | 1.0 |
| 7. Dipropylene glycol | 5.0 | 5.0 | 5.0 | 5.0 | 5.0 | 5.0 | 5.0 | 5.0 |
| 8. Xanthan gum | 0.3 | 0.3 | 0.3 | 0.3 | 0.3 | 0.3 | 0.3 | 0.3 |
| 9. 2-Palmitoyl-3-glyceryl phosphoryl choline | 0.01 | 0.1 | 0.5 | 1.0 | 5.0 | 10.0 | 1.0 | — |
| 10. Methyl-p-oxybenzoate | 0.2 | 0.2 | 0.2 | 0.2 | 0.2 | 0.2 | 0.2 | 0.2 |
| 11. Perfume | 0.1 | 0.1 | 0.1 | 0.1 | 0.1 | 0.1 | 0.1 | 0.1 |
| 12. Purified water | 80.79 | 80.7 | 80.3 | 79.8 | 75.8 | 70.8 | 80.8 | 80.8 |
| Storage stability I.A.P. | 1600 | 1750 | 1800 | 2000 | 1900 | 2200 | 1800 | 1200 |
| (viscosity, cps) 0° C., 3 months | 5000 | 3800 | 3500 | 3600 | 3400 | 3800 | 17000 | 4000 |
| 45° C., 3 months | 400 | 1800 | 2300 | 2200 | 2300 | 2000 | 300 | separation |
| Evaluation | G | VG | VG | VG | VG | G | SG | Bad |
| Organoleptic properties | G | G | VG | VG | VG | G | *1 | *2 |
| Appearance (texture) | G | G | G | G | G | G | SG | *3 |

I.A.P.: Immediately After Preparation, G: Good, VG: Very Good, SG: Slightly Good
*1: Less smoothness, *2: No smoothness, *3: Rough texture

EXAMPLES 18 TO 23 AND COMPARISON EXAMPLES 8 AND 9

Skin creams were prepared with the formulations shown in Table 4 (part by weight).

1-Stearoyl-3-glyceryl phosphoryl ethanolamine and 1-stearoyl-2-palmitoyl-3-glyceryl phosphoryl inositol were used as monoacyl phosphatide and diacyl phosphatide, respectively.

The oily ingredients 1 to 7 shown in the Table were mixed to dissolve homogeneously at about 80° C. (solution 1). The water-soluble ingredients 8 to 10 and 12 were mixed to dissolve homogeneously at about 80° C. (solution 2). Solution 1 was added to solution 2 under stirring with a homomixer to emulsify, and then cooled. During this cooling step, ingredient 11 was added at a temperature of 70° C. When the temperature lowered to 30° C., the stirring was stopped.

The properties of the resulting skin milks are as shown in Table 4.

The skin creams of Examples 18 to 23 showed excellent storage stability, organoleptic properties and appearance. In contrast, the skin creams of Comparisons 8 and 9 which lacked either one of monoacyl phosphatide or diacyl phosphatide caused phase separation during the storage at 45° C. for 1 month or after the storage at 45° C. for 3 days, respectively. Thus, these had a problem with storage stability. The skin creams of the invention were highly superior to the Comparison Examples in all of the storage stability, organoleptic properties and appearance.

TABLE 4

|  | Ex. 18 | Ex. 19 | Ex. 20 | Ex. 21 | Ex. 22 | Ex. 23 | Comp. 8 | Comp. 9 |
|---|---|---|---|---|---|---|---|---|
| 1. Olive oil | 5.0 | 5.0 | 5.0 | 5.0 | 5.0 | 5.0 | 5.0 | 5.0 |
| 2. Liquid paraffin | 15.0 | 15.0 | 15.0 | 15.0 | 15.0 | 15.0 | 15.0 | 15.0 |
| 3. Bees wax | 2.0 | 2.0 | 2.0 | 2.0 | 2.0 | 2.0 | 2.0 | 2.0 |
| 4. Cetyl alcohol | 8.0 | 8.0 | 8.0 | 8.0 | 8.0 | 8.0 | 8.0 | 8.0 |
| 5. Glyceryl monostearate | 3.0 | 3.0 | 3.0 | 3.0 | 3.0 | 3.0 | 3.0 | 3.0 |
| 6. White vaseline | 3.0 | 3.0 | 3.0 | 3.0 | 3.0 | 3.0 | 3.0 | 3.0 |
| 7. 1-Stearoyl-2-palmitoyl-3-glyceryl phosphoryl inositol | 0.001 | 0.01 | 0.1 | 0.5 | 5.0 | 10.0 | — | 1.0 |
| 8. Sorbltol | 10.0 | 10.0 | 10.0 | 10.0 | 10.0 | 10.0 | 10.0 | 10.0 |
| 9. 1-Stearoyl-3-glyceryl phosphoryl ethanolamine | 0.5 | 0.5 | 0.5 | 0.5 | 0.5 | 0.5 | 0.5 | — |
| 10. Methyl p-oxybenzoate | 0.2 | 0.2 | 0.2 | 0.2 | 0.2 | 0.2 | 0.2 | 0.2 |
| 11. Perfume | 0.1 | 0.1 | 0.1 | 0.1 | 0.1 | 0.1 | 0.1 | 0.1 |
| 12. Purified water | 53.199 | 53.19 | 53.1 | 52.7 | 48.2 | 43.2 | 53.2 | 52.7 |
| Storage stability 45° C. | S3 | S3 | S4 | S4 | S4 | S4 | *1 | *2 |
| 0° C. | S5 | S6 | S6 | S6 | S6 | S5 | S3 | *3 |
| Evaluation | G | VG | VG | VG | VG | G | SG | Bad |
| Organoleptic properties | G | VG | VG | VG | VG | G | *4 | *5 |
| Appearance (texture) | G | VG | VG | VG | VG | G | SG | *6 |

S3, S4, S5 and S6: Stable after 3, 4, 5 or 6 months, respectively
*1: Separated after 1 month, *2: Separated after 3 days, *3: Solidified after 1 month
G: Good, VG: Very Good, SG: Slightly Good, *4: Less smoothness, *5: No smoothness, *6: Rough texture

EXAMPLE 24

A make-up base was prepared with the following formulation (part by weight).

2-Palmitoyl-3-glyceryl phosphoryl inositol and 1-stearoyl-3-glyceryl phosphoryl choline were used as monoacyl phosphatide. 1,2-dioleoyl-3-glyceryl phosphoryl choline and 1-palmitoyl-2-stearoyl-3-glyceryl phosphoryl ethanolamine were used as diacyl phosphatide.

| | |
|---|---|
| 1. Liquid paraffin | 12.0 |
| 2. Squalane | 3.0 |
| 3. Glyceryl monostearate | 1.5 |
| 4. Cholesterol | 0.2 |
| 5. Cetyl alcohol | 0.3 |
| 6. 1,2-Dioleoyl-3-glyceryl phosphoryl choline | 1.0 |
| 7. 1-Palmitoyl-2-stearoyl-3-gyceryl phosphoryl ethanolamine | 0.5 |
| 8. Glycerin | 5.0 |
| 9. Carrageenan | 0.5 |
| 10. 2-Palmitoyl-3-glyceryl phosphoryl inositol | 0.4 |
| 11. 1-Stearoyl-3-glyceryl phosphoryl choline | 0.1 |
| 12. Methyl p-oxybenzoate | 0.1 |
| 13. Dipropylene glycol | 3.0 |
| 14. Titanium oxide | 0.5 |
| 15. Perfume | 0.1 |
| 16. Purified water | 71.8 |

Among the above ingredients, the oily ingredients 1 to 7 were mixed to dissolve homogeneously at about 80° C. (solution 1). The water-soluble ingredients 8 to 12 and 16 were mixed to dissolve homogeneously at about 80° C. (solution 2). Ingredient 14 was uniformly dispersed in ingredient 13 (dispersion 3). To solution 2 under stirring with a homomixer, solution 1 was added to emulsify and then the dispersion 3 was added, followed by further stirring and cooling.

During this cooling step, ingredient 15 was added at a temperature of 70° C. When the temperature lowered to 30° C., the stirring was stopped.

The make-up base thus obtained of Example 24 was an O/W emulsion and was very stable after stored in a thermostatic chamber at 45° C. for 4 months. It was also very stable after storage at 0° C. or 5° C. for 6 months, and showed good organoleptic properties and appearance (texture).

As described above, the cosmetic composition according to the invention shows very good storage stability at high and low temperatures and, in addition, has very good organoleptic properties and appearance.

What we claim is:

1. A cosmetic composition which comprises a solution of water; from 0.0001 to 1.0 weight % of a higher fatty acid; and from 0.01 to 10 weight % of a monoacyl phosphatide represented by the following general formula

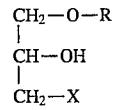

wherein R represents

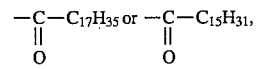

and X represents

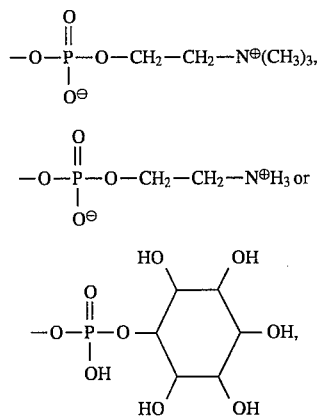

and from 0.01 to 10 weight % of a saponin compound selected from the group consisting of a saponin composed of a sterol and a saccharide moiety, a saponin composed of a triterpene moiety and a saccharide moiety, and mixtures thereof, the moieties being bound by glycosidic linkage.

2. The cosmetic composition according to claim 1, wherein the saponin is one obtained by extraction from licorice, pericarp of *Sapindus mukurosii*, soyabean, rhizome of *Sanguisorba officinalis L.*, seed of *Thea sinensis, L.* or seed of camellia.

3. The cosmetic composition according to claim 1, wherein the saponin is added in the form of an unpurified saponin-containing plant extract.

4. The cosmetic composition according to claim 1, wherein the saponin and the monoacyl phosphatide are each contained in an amount of about 0.1 to 5% by weight, based on the total weight of the cosmetic composition.

5. The cosmetic composition according to claim 1 wherein the monoacyl phosphatide is contained in amounts of about 0.1 to 5% by weight based on the total weight of the cosmetic composition.

6. The cosmetic composition according to claim 1, wherein the cosmetic composition is a clear skin treatment lotion.

* * * * *